United States Patent
Schulze Nahrup et al.

(10) Patent No.: US 8,309,607 B2
(45) Date of Patent: Nov. 13, 2012

(54) RAPID RELEASE IRBESARTAN-CONTAINING PHARMACEUTICAL COMPOSITION

(75) Inventors: Julia Schulze Nahrup, Neuried (DE); Sandra Brueck, Ottenhofen (DE); Rainer Alles, Müchen (DE); Peter Kraass, Bad Krozingen (DE)

(73) Assignee: ratiopharm GmbH, Ulm (DE)

( * ) Notice: Subject to any disclaimer, the term of this patent is extended or adjusted under 35 U.S.C. 154(b) by 784 days.

(21) Appl. No.: 12/279,062

(22) PCT Filed: Feb. 13, 2007

(86) PCT No.: PCT/DE2007/000301
§ 371 (c)(1),
(2), (4) Date: Nov. 20, 2008

(87) PCT Pub. No.: WO2007/093168
PCT Pub. Date: Aug. 23, 2007

(65) Prior Publication Data
US 2009/0220597 A1   Sep. 3, 2009

(30) Foreign Application Priority Data

Feb. 13, 2006   (DE) .................. 10 2006 006 588

(51) Int. Cl.
*A01N 41/06* (2006.01)
*A01N 43/64* (2006.01)
*A61K 31/18* (2006.01)
*A61K 31/41* (2006.01)

(52) U.S. Cl. ........................ 514/601; 514/381
(58) Field of Classification Search .............. 514/601, 514/381
See application file for complete search history.

(56) References Cited

U.S. PATENT DOCUMENTS

| | | | | |
|---|---|---|---|---|
| 5,856,362 | A | * | 1/1999 | Hudson .................. 514/682 |
| 5,994,348 | A | * | 11/1999 | Ku et al. .................. 514/223.5 |
| 6,559,134 | B2 | * | 5/2003 | Tanno et al. .................. 514/57 |
| 2001/0010825 | A1 | * | 8/2001 | Shimizu et al. ............... 424/465 |
| 2002/0076437 | A1 | * | 6/2002 | Kothari et al. ................ 424/465 |

FOREIGN PATENT DOCUMENTS

| | | |
|---|---|---|
| EP | 1 275 391 A1 | 1/2003 |
| EP | 1 806 130 A1 | 7/2007 |
| WO | WO 2006/013545 A1 | 2/2006 |

OTHER PUBLICATIONS

International Search Report issued by the European Patent Office for PCT/DE2007/000301 (Aug. 6, 2007).

* cited by examiner

*Primary Examiner* — Benjamin Packard
(74) *Attorney, Agent, or Firm* — Chalin A. Smith; Smith Patent Consulting (57) ABSTRACT

The present invention relates to an irbesartan-containing pharmaceutical composition, in particular a tablet thereof, which comprises the active ingredient, a disintegrant with at least one low-substituted hydroxypropyl cellulose.

14 Claims, 4 Drawing Sheets

RAPID RELEASE IRBESARTAN-CONTAINING PHARMACEUTICAL COMPOSITION

This application corresponds to the national phase of PCT Application No. PCT/DE2007/000301, filed Feb. 13, 2007, which, in turn, claims priority to German Patent Application No. 10 2006 006 588.3, filed Feb. 13, 2006, the contents from both of which are incorporated by reference herein in their entirety.

The present invention relates to a rapid release irbesartan-containing pharmaceutical composition, in particular a rapid release irbesartan-containing tablet.

Irbesartan, 2-n-butyl-4-spirocyclopentane-1-[(2'-(tetrazol-5-yl)biphenyl-4-yl)methyl]-2-imidazolin-5-one, is a known angiotensin II antagonist. It is used in particular in cardiac and vascular problems, such as hypertension and cardiac insufficiency, as well as in disorders of the central nervous system and in the treatment of glaucoma, diabetic retinopathy and renal insufficiency. Irbesartan which has the following structure (I)

comes under the general formula of U.S. Pat. No. 5,270,317.

WO-A-91/14679 discloses irbesartan for use in the treatment of hypertension and heart failure.

Irbesartan can be available in several polymorphous forms. Polymorphous forms A and B are described in EP 0 708 103 and DE 695 19 788. WO 03/050110 discloses an amorphous form of irbesartan.

Irbesartan has an acceptable oral bioavailability but an unpleasant taste so that an administration in dissolved form, such as in the form of a syrup, is unfavorable. A preferred form of administration is therefore a tablet which contains a substantial amount of irbesartan as active ingredient. The dissolution profile of the tablet is a critical parameter for the administration of irbesartan. The tablet should ensure a rapid and complete release of the active ingredient. In particular, the dissolution profile shall not deteriorate even during long storage times of the tablet, i.e. even after storage, the active ingredient shall still be released very rapidly while dissolving.

However, it is difficult to formulate irbesartan as a rapid release tablet since it has poor flow characteristics and only a minor aqueous solubility. EP-A 747 050 describes the difficulties in the production of a rapid release irbesartan tablet. According to this publication, the tablet is to have a dissolution performance such that 80% or more of the irbesartan or a salt thereof contained in the tablet dissolves within 30 minutes.

In order to obtain such a release performance, EP-A 747 050 considers it necessary to formulate irbesartan together with a surfactant, in particular a poloxamer, into tablets. However, the required use of a surfactant restricts the formulation scientist's freedom of action, and it would be favorable to have a rapid release irbesartan tablet which does not necessarily contain a surfactant. Moreover, the tablets produced according to EP 747 050 can still be improved since the release of irbesartan from these tablets decreases when the tablets are stored.

Applicant of EP-A 747 050 has currently a rapid release irbesartan tablet entitled APROVEL® on the market. This product exhibits a rapid release, yet the release of this current market product also deteriorates (i.e. the release slows down) after the storage of the tablets, which is undesired.

Therefore, it is the object of the present invention to provide a pharmaceutical composition, in particular a tablet, which has a high irbesartan content, enables a rapid release of irbesartan and does not have the problems of the prior art tablets. In particular, the object is to provide an irbesartan-containing tablet which enables a rapid release of the active ingredient, such as irbesartan, even after prolonged storage times and in which the storage changes the release profile as little as possible.

According to the invention it has been found that this object is achieved by a pharmaceutical composition, in particular a tablet, having a special mixture of disintegrants.

Thus, the present invention relates to a pharmaceutical composition, in particular a tablet, which comprises 20 to 90% by weight, in particular 50 to 90% by weight, preferably 60 to 85% by weight, in particular 60 to 80% by weight, more preferably 60 to 70% by weight, e.g. about 65% by weight, of irbesartan or a pharmaceutically acceptable salt thereof and at least 5% by weight, preferably at least 10% by weight, more preferably at least 15% by weight, in particular at least 20% by weight, such as at least 25% by weight, of disintegrant, at least 40% by weight, preferably at least 50% by weight, in particular about 60% by weight or more, more preferably about 70% by weight, most preferably about 80% by weight or more of the disintegrant being low-substituted hydroxypropyl cellulose.

It is preferred to use irbesartan having an average particle size of less than or equal to 100 μm, more preferably less than or equal to 10 μm, in particular in the range of 1 to 5 μm.

Irbesartan can be available in the pharmaceutical compositions according to the invention in any polymorphous or amorphous form or in a mixture of such forms, in particular in polymorphous form A or polymorphous form B or a mixture thereof and, where appropriate, also in admixture with the amorphous form. It is particularly preferred for irbesartan to be available in polymorphous form A (as described in EP 708 103 and DE 695 19 788).

Where appropriate, irbesartan can be available in admixture with a diuretic as described in EP-A-1 275 391, for example, in particular with hydrochlorothiazide.

If such a diuretic is contained in the pharmaceutical composition according to the invention, it is preferably included in an amount of 2 to 33% by weight. In this case, the irbesartan amount is preferably 20 to 70% by weight, more preferably about 50% by weight, the total amount of the active ingredient combination constituting no more than 90% by weight, more preferably no more than 85% by weight, of the pharmaceutical composition.

The low-substituted hydroxypropyl cellulose fraction of the disintegrant is usually no more than 95% by weight, preferably no more than 90% by weight, in particular no more than 85% by weight. The disintegrant of the pharmaceutical composition (of the medicament) therefore comprises preferably 40 to 95%, more preferably 50 to 90%, even more preferably 60 to 90%, in particular 70 to 90% by weight, in particular 80 to 90% by weight, of low-substituted hydroxypropyl cellulose, the rest of the disintegrant representing one or several further disintegrants other than low-substituted hydroxypropyl cellulose. A typical ratio is about 84% low-substituted hydroxypropyl cellulose to about 16% further disintegrant.

Preferred low-substituted hydroxypropyl celluloses are available e.g. from the Shin Etsu company under the designation of L-HPC. The hydroxypropyl content of low-substituted hydroxypropyl cellulose usually ranges from 5 to 16%, preferably from 8 to 15%, in particular from 10.0 to 12.9%. The most preferred products, L-HPC LH-11 and L-HPC LH-21, have a hydroxypropyl content of about 10.0 to 12.9%.

For a more accurate definition of the preferred low-substituted hydroxypropyl cellulose, reference can be made to USP (National Formulary) and in particular also to the entry under the keyword L-HPC in the standard reference book by Fiedler, *Lexikon der Hilfsstoffe für Pharmazie, Kosmetik und angrenzende Gebiete* [dictionary of excipients used in pharmacy, cosmetics and adjacent fields], 5$^{th}$ edition 2002, as well as to the brochures of Shin Etsu or the "Handbook of Excipients", edited by the America Pharmaceutical Association and Dr. Arthur H. Kibbe, 3$^{rd}$ edition 2000. Low-substituted hydroxypropyl cellulose is used as both binder and disintegrant, as described in Schmidt Christin, *Wirk-und Hilfsstoffe für Rezeptur, Defektur und Großherstellung* [active ingredients and excipients for formulations, small-scale and large-scale productions], Stuttgart 1999. Based on this application, low-substituted hydroxypropyl cellulose is counted among the disintegrants and not the binders.

The low-substituted hydroxypropyl cellulose L-HPC is sold under the classifications LH-11, LH-20, LH-21, LH-22, LH-30, LH-31 and LH-32, for example. Types LH-11 and LH-21, in particular LH-21, are preferred according to the invention.

It is preferred to use the low-substituted hydroxypropyl celluloses having small and medium particle sizes, preferably in the range of 30 to 100 μm, more preferably from 30 to 60 μm, in particular from 40 to 50 μm, such as L-HPC LH-11 (about 50 μm) and L-HPC LH-21 (about 40 μm).

A type of low-substituted hydroxypropyl celluloses or a mixture of different low-substituted hydroxypropyl celluloses can be used according to the invention.

The content of low-substituted hydroxypropyl cellulose in the medicament is usually 4 to 30%, preferably 6 to 27%, more preferably 10 to 25% or 15 to 25% (each based on the total weight of the medicament). Contents of 6 to 14% and 10 to 12% (each based on the total weight of the medicament) are also preferred.

Along with low-substituted hydroxypropyl cellulose, the medicament according to the invention usually has at least one further disintegrant, preferably at least 5%, in particular at least 10%, more preferably at least 15%, based on the total weight of the available disintegrants. The content of further disintegrant (i.e. disintegrant which is no low-substituted hydroxypropyl cellulose) in the medicament is preferably 1 to 6%, more preferably 1.5 to 5.5%, in particular 2 to 5% or 3 to 5% or 4 to 5% (each based on the total weight of the medicament).

The further disintegrants are not particularly limited. The conventional disintegrants with which a person skilled in the art is familiar can be used for this purpose. The disintegrants listed in the above cited standard work by Fiedler under the keyword "Tabletten-Sprengmittel [tablet disintegrants]" are preferred. Preferred further disintegrants are alginic acid, sodium alginate, cellulose derivatives, such as sodium carboxymethyl cellulose and sodium croscarmellose, crospovidone, pregelatinized starch, sodium starch glycolate or starch. The disintegrants known as "super disintegrants" and in particular sodium carboxymethyl cellulose and sodium croscarmellose are most preferred.

Some disintegrants are also used as binders. If a preparation which is not assigned expressly to a group in this application can be used as both disintegrant and binder, it is counted among the disintegrants and not among the binders according to the invention unless otherwise expressly mentioned or obvious under the circumstances.

Furthermore, the medicament according to the invention may contain further additives and excipients and, where appropriate, coating agents known to the person skilled in the art, and in this respect reference can again be made to the standard reference book by Fiedler or the "Handbook of Excipients", for example.

In particular, the irbesartan-containing pharmaceutical composition can comprise one or several fillers, binders, flow regulating agents, lubricants or surfactants, in particular 0 to 20% by weight of filler, 0 to 5% by weight of binder, 0 to 3% by weight of flow regulating agent, 0 to 2% by weight of lubricant and 0 to 2% by weight of surfactant. The other conventional additives and excipients and, where appropriate, coating agents are available in a total amount so as to yield 100% for the pharmaceutical composition according to the invention.

One or several compounds which represent part of the material for achieving the required total tablet composition can be used as a filler. Preferred fillers are inorganic phosphates, such as dibasic calcium phosphate, or sugar or sugar-like substances and the derivatives thereof, in particular lactose, such as lactose monohydrate or anhydrous lactose, dextrose, sorbitol, mannitol, saccharose, maltodextrin, isomalt and tablettose. Cellulose, such as microcrystalline cellulose or powdered cellulose, are also counted among the fillers according to the invention. In a preferred embodiment, the pharmaceutical composition according to the invention contains no fillers.

The binder is one or several compounds enabling the granulation of irbesartan and/or the other ingredients into larger, denser particles. Preferred binders are gelatin, povidone (an N-vinylpyrrolidone polymer), hydroxypropylmethyl cellulose and in particular copovidone (a copolymer of N-vinyl-2-pyrrolidone and vinyl acetate, e.g. plasdone S-630 or collidone VA64).

In the compositions of the present invention, the flow regulating agent is one or several compounds improving the flow characteristics of the pharmaceutical composition. Preferred flow regulating agents are silicon dioxide or magnesium trisilicate, e.g. Aerosil type 200 or talcum.

One or several compounds supporting the production and processing of the tablets serve as a lubricant. Preferred lubricants are fatty acids or fatty acid derivatives, such as alkaline and alkaline earth salts of stearic, lauric and/or palmitic acid, as well as glycerylmonostearate or glycerotristearate, glycerylpalmitostearate, sodium lauryl sulfate, sodium stearyl fumarate, zinc stearate, hydrogenated vegetable oils (lubritab), sodium benzoate, polyethylene glycol or talc, with sodium stearyl fumarate and magnesium stearate being preferred.

Although unlike the irbesartan-containing pharmaceutical preparations of the prior art, the pharmaceutical compositions according to the invention do not necessarily have to contain a surfactant, such a surfactant can, of course, be included in the pharmaceutical compositions according to the invention.

The surfactant included in the irbesartan-containing pharmaceutical composition, where appropriate, can be a poloxamer or polysorbate, for example. A polysorbate, in particular polysorbate 80, such as the commercial Tween 80, is preferred.

The medicament according to the invention preferably contains no sodium lauryl sulfate as the surfactant.

According to the invention, the pharmaceutical composition is preferably a tablet which can be produced as usual by granulation or direct compression. The tablet according to the invention preferably has a release profile so as to release 80% by weight or more of the irbesartan compound contained in the tablet within 30 minutes, more preferably within 15 minutes. Another preferred release profile of the tablet according to the invention is such that 90% by weight or more of the irbesartan compound in the tablet is released within 30 minutes and 80% by weight or more (preferably 90% by weight or more) of the irbesartan compound in the tablet is released within 15 minutes.

It is particularly preferred for a tablet according to the invention to have such a release profile as defined above even after 3, and more preferably after 6, months of storage in a closed glass container under extreme conditions, i.e. at 40° C. and 75% relative humidity.

It is particularly preferred for the irbesartan part which is released within 30 minutes or within 15 minutes to be reduced by no more than 30%, more preferably by no more than 20%, in particular by no more than 10%, more preferably by no more than 5%, most preferably by no more than 2% as a result of the 3-month storage under the above mentioned extreme conditions.

The irbesartan-containing pharmaceutical composition of the present invention can be available as a tablet which can be film-coated with one or several coating agents. The coating agents are not particularly limited and are known to the person skilled in the art. In so far as reference is made in the present application to a release profile this is a release profile of the uncoated tablet or the tablet core unless otherwise expressly indicated or evident from the context.

The active ingredient of the pharmaceutical composition of the present invention is irbesartan which may be available in neutral form or as a pharmaceutically acceptable salt, preferably irbesartan of polymorphous form A.

Based on the present invention, "release profile" is understood to mean the temporal course related to the irbesartan amount which is available in dissolved form, based on the entire irbesartan quantity. This release profile is obtained by dissolving a tablet in an USP apparatus II in 900 ml 0.1 M hydrochloric acid at 37° C. and a stirring speed of 50 rpm and measuring the dissolved irbesartan amount over a period, e.g. one hour, at various points of time, e.g. every five minutes, the absorption of the U.V. light at 244 nm serving as a measured value.

The tablets comprising the irbesartan-containing pharmaceutical composition according to the invention are preferably made such that the low-substituted hydroxypropyl cellulose is initially fully or partially mixed with irbesartan, this mixture is then granulated with a binder and the rest of the disintegrants and the other excipients are then mixed with the granulate and this mixture is compressed into tablets. The following method is particularly preferred:
1. mixing irbesartan, a low-substituted hydroxypropyl cellulose, e.g. L-HPC 21 and, where appropriate, flow regulating agent,
2. granulating the mixture with an aqueous binder solution, e.g. a 3 to 10% aqueous copovidone solution and, where appropriate, the surfactant, preferably in a high-shear mixer,
3. sieving the granulate,
4. adding the rest of the constituents, such as, where appropriate, a second low-substituted hydroxypropyl cellulose, e.g. L-HPC 11, and/or, where appropriate, another part of the first low-substituted hydroxypropyl cellulose, where appropriate, further flow regulating agent, and also disintegrant and, where appropriate, a lubricant, followed by mixing,
5. compressing the mixture into tablets,
6. film-coating the tablets, where appropriate, with one or several coating agents.

In a preferred embodiment of the present invention, the tablets according to the invention contain 75 to 300 mg, e.g. 75, 150 or 300 mg, irbesartan.

The percentages based on this application refer to the weight, unless otherwise expressly indicated or obvious to the person skilled in the art. When the weight of a tablet is the reference parameter, it refers to the weight of the uncoated tablet or the weight of the tablet core, unless otherwise indicated or obvious to the person skilled in the art.

The below examples explain the invention:

EXAMPLE 1

An irbesartan-containing tablet according to the invention was produced from the following components:

| No. | Component | Mass in mg | Mass in % |
|---|---|---|---|
| 1 | Irbesartan (polymorph A) | 300 | 80.8 |
| 2 | L-HPC LH 21 | 20.6 | 5.55 |
| 3 | Copovidone | 12.8 | 3.4 |
| 4 | L-HPC LH 11 | 20.6 | 5.55 |
| 5 | Aerosol type 200 | 1 | 0.27 |
| 6 | Sodium starch glycolate | 12.3 | 3.3 |
| 7 | Sodium stearyl fumarate | 4 | 1.1 |

The components were processed as follows:
1. Mixing (1) and (2),
2. wet-granulating the mixture with an 8% aqueous copovidone solution (3) in a high-shear mixer,
3. sieving the moist granulate,
4. adding (4) to (7) and mixing them with the granulate,
5. compressing the mixture into tablets,
6. film-coating the tablets with a Eudragit EPO film and then with an HPMC film.

Figure 1:
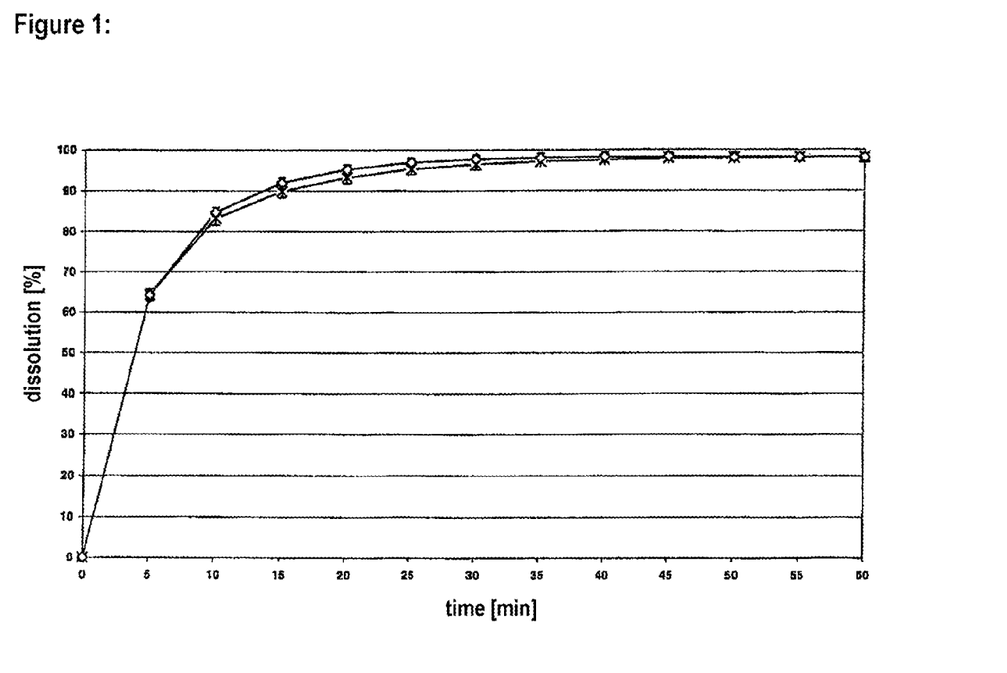
FIG. 1: Release profile of an inventive tablet according to Example 1, containing 300 mg irbesartan, shortly after the production (X) and after 3-month storage at 40° C. and 75% relative humidity (◇) in a closed glass container.

The tablets obtained in Example 1 were subjected to a release test prior to the film coating step, and the release profile was determined as indicated above. A sample of the uncoated tablets was stored in a closed glass container at 40° C. and 75% relative humidity for 3 months, and then the release profile was determined. The result of the experiments is shown in FIG. 1. The tablet releases irbesartan very rapidly and the release is virtually not impaired by the storage of the medicament.

COMPARATIVE EXAMPLE 1

Figure 2:
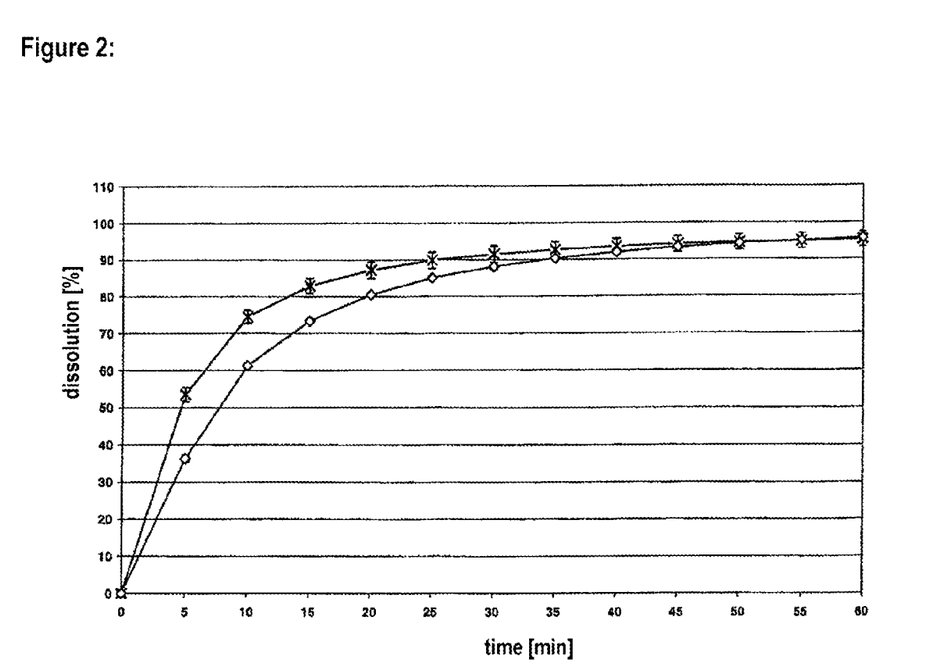
FIG. 2: Release profile of a APROVEL® tablet (commercial product, as presently sold in Canada, for example, 300 mg irbesartan), shortly after the production (X) and after 3-month storage at 40° C. and 75% relative humidity (◇) in a closed glass container (Comparative Example 1).

A commercial APROVEL® tablet—as presently sold in Canada, for example—having the following components: irbesartan (300 mg), microcrystalline cellulose, sodium croscarmellose, lactose monohydrate, magnesium stearate, silicon dioxide hydrate, corn starch, poloxamer 188, was analyzed as indicated in Example 1. The result is shown in FIG. 2. The release of irbesartan from the tablet prior to storage is already poorer than the release of irbesartan from the tablets according to the invention. The release becomes even worse by storage.

EXAMPLE 2

Irbesartan-containing tablets according to the invention were produced form the following components:

| No. | Component | Mass in mg | Mass in mg | Mass in mg |
|---|---|---|---|---|
| 1 | Irbesartan (polymorph A) | 75.00 | 150.00 | 300.0 |
| 2 | Low-substituted hydroxypropyl cellulose (L-HPC), LH 21 | 27.37 | 54.73 | 109.45 |
| 3 | Aerosil 200 | 0.75 | 1.50 | 3.00 |
| 4 | Copovidone, collidone VA 64 | 4.00 | 8.00 | 16.00 |
| 5 | Croscarmellose sodium Ac-Di-Sol | 5.50 | 10.99 | 21.98 |
| 6 | Aerosil 200 | 0.35 | 0.69 | 1.37 |
| 7 | Sodium stearyl fumarate, Pruv | 1.00 | 2.00 | 4.00 |
| 8 | Total | 113.97 | 227.91 | 455.8 |

The components were processed as follows:

1. Mixing the constituents (1), (2) and (3)
2. wet-granulating the mixture with a 5% aqueous solution of (4)
3. sieving the granulate
4. adding the components (5), (6) and (7) and mixing them with the granulate
5. compressing the mixture into tablets.

Figure 3:
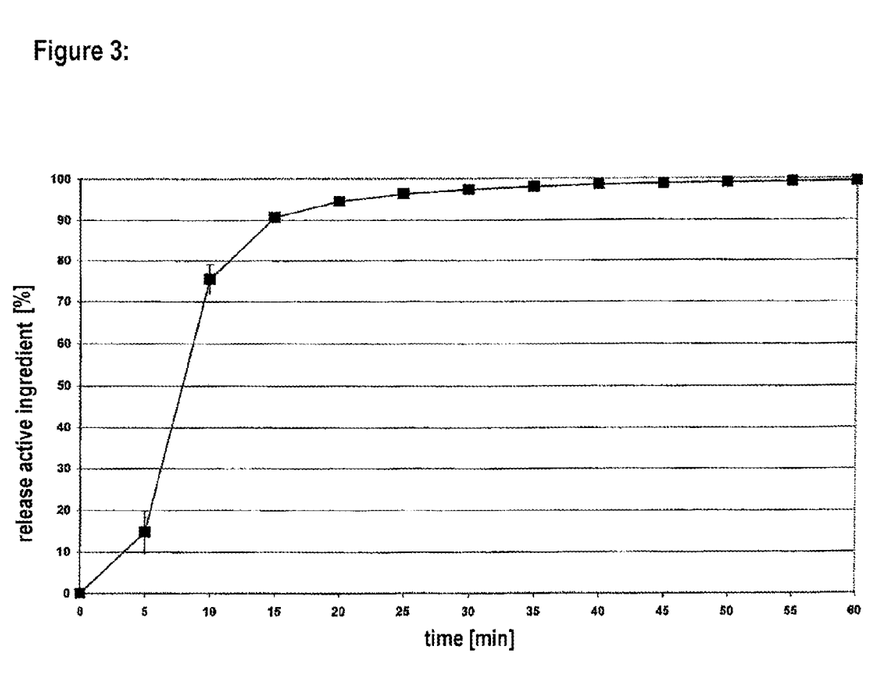
FIG. 3: Release profile of an inventive tablet according to Example 2 (300 mg irbesartan).

The tablet containing 300 mg irbesartan was subjected to a release test and the release profile was determined as indicated above. The result is shown in FIG. 3. The tablets can be coated with an "Opadry II white" coating system of Colorcon company, for example. The coating system substantially contains polyvinyl alcohol, titanium dioxide, polyethylene glycol and talc. The coating constitutes about 1% of the tablet weight (e.g. 4.33 mg=0.94% of the tablet containing 300 mg active ingredient).

EXAMPLE 3

Irbesartan-containing tablets according to the invention were produced from the following components:

| No. | Constituent | Mass in mg | Mass in mg | Mass in mg |
|---|---|---|---|---|
| 1 | Irbesartan (polymorph A) | 75.00 | 150.00 | 300.0 |
| 2 | Low-substituted hydroxypropyl cellulose (L-HPC), LH 21 | 27.37 | 54.73 | 109.45 |
| 3 | Aerosil 200 | 0.75 | 1.50 | 3.00 |
| 4 | Copovidone, collidone VA 64 | 4.00 | 8.00 | 16.00 |
| 5 | Polysorbate 80 Tween 80 | 1.00 | 2.00 | 4.00 |
| 6 | Croscarmellose sodium Ac-Di-Sol | 5.50 | 10.99 | 21.98 |
| 7 | Aerosil 200 | 0.35 | 0.69 | 1.37 |
| 8 | Sodium stearyl fumarate, Pruv | 1.00 | 2.00 | 4.00 |
| 9 | Total | 114.97 | 227.91 | 459.8 |

The components were processed as follows:
6. mixing the components (1), (2) and (3)
7. wet-granulating the mixture with a 5% aqueous solution of (4) and (5)
8. sieving the granulate
9. adding the components (6), (7) and (8) and mixing them with the granulate
10. compressing the mixture into tablets.

Figure 4:
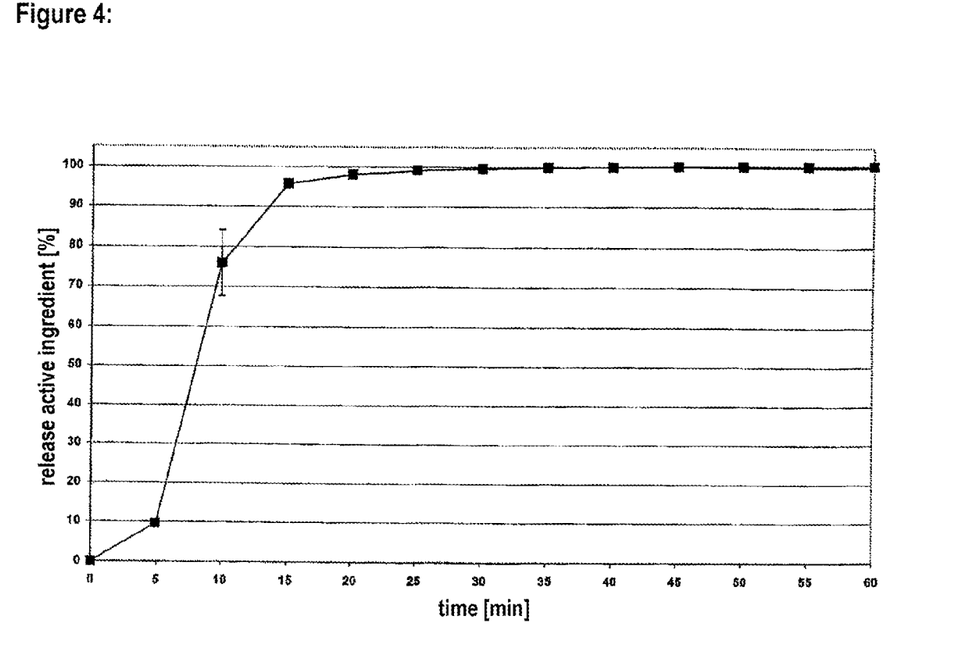
FIG. 4: Release profile of an inventive tablet according to Example 3 (300 mg irbesartan).

The tablet containing 300 mg irbesartan was subjected to a release test, and the release profile was determined as indicated above. The result is shown in FIG. 4. The tablets can be coated with an "Opadry II white" coating system of Colorcon company, for example. The coating system contains substantially polyvinyl alcohol, titanium dioxide, polyethylene glycol and talc. The coating constitutes about 1% of the tablet weight (e.g. 4.33 mg=0.93% of the tablet containing 300 mg active ingredient).

The invention claimed is:

1. A pharmaceutical composition, comprising 50-85% by weight of irbesartan or a pharmaceutically acceptable salt thereof and at least 15% by weight of a disintegrant, at least 40% by weight of the disintegrant being low-substituted hydroxypropyl cellulose that comprises 8 to 15% by weigh hydroxylpropyl groups.

2. The pharmaceutical composition according to claim 1, wherein at least 60% by weight of the disintegrant is low-substituted hydroxypropyl cellulose.

3. The pharmaceutical composition according to claim 1, wherein the low-substituted hydroxypropyl cellulose is L-HPC LH-11, L-HPC LH-21 or a mixture thereof.

4. The pharmaceutical composition according to claim 1, further comprising a diuretic as another active ingredient.

5. The pharmaceutical composition according to claim 1, further comprising one or several excipients selected from the group consisting of fillers, binders, flow regulating agents, lubricants and surfactants.

6. The pharmaceutical composition according to claim 5, wherein said composition contains
    0-20% by weight of filler,
    0-5% by weight of binder,
    0-3% by weight of flow-regulating agent,
    0-2% by weight of lubricant,
    0-2% by weight of surfactant.

7. The pharmaceutical composition according to claim 5, further comprising a surfactant.

8. The pharmaceutical composition according to claim 7, wherein said surfactant is a polysorbate.

9. The pharmaceutical composition according to claim 1, wherein said composition is a tablet.

10. The pharmaceutical composition according to claim 9, wherein said tablet exhibits a dissolution profile such that 80% or more of the irbesartan compound contained in the tablet dissolves within 15 minutes.

11. The pharmaceutical composition according to claim 10, wherein said tablet exhibits a release profile after 3-month, closed storage at 40° C. and 75% relative humidity such that 80% or more of the irbesartan compound contained in the tablet dissolves within 15 minutes.

12. The pharmaceutical composition according to claim 9, wherein said tablet is a film tablet.

13. A method of producing a pharmaceutical composition according to claim 1, said method comprising the steps of initially mixing and granulating the irbesartan with at least one part of the low-substituted hydroxypropyl cellulose, mixing the granulate with the other components, and compressing the resulting mixture into tablets.

14. The method of claim 13, said method further comprising the step of providing said tablets with a film-coating.

* * * * *

UNITED STATES PATENT AND TRADEMARK OFFICE
CERTIFICATE OF CORRECTION

| | |
|---|---|
| PATENT NO. | : 8,309,607 B2 |
| APPLICATION NO. | : 12/279062 |
| DATED | : November 13, 2012 |
| INVENTOR(S) | : Julia Schulze-Nahrup et al. |

It is certified that error appears in the above-identified patent and that said Letters Patent is hereby corrected as shown below:

On the title page, item (75) (Inventors), after "Sandra Brueck", replace the term "Ottenhoffen" with -- Muenchen --.

On the title page, item (75) (Inventors), after "Rainer Alles", replace the term "Müchen" with -- Muenchen --.

In column 7, line 33, after "3", replace the term "Aerosol 200" with -- Aerosil ® 200 --.

In column 7, lines 34-35, after "4 Covipodone", replace the term "collidone VA 64" with -- Kollidon ® VA 64 --.

In column 7, line 38, after "6", replace the term "Aerosol 200" with -- Aerosil ® 200 --.

In column 8, line 9, after "3", replace the term "Aerosil 200" with -- Aerosil ® 200 --.

In column 8, lines 10-11, after "4 Covipodone", replace the term "collidone VA 64" with -- Kollidon ® VA 64 --.

In column 8, line 13, after "6", replace the term "Aerosol 200" with -- Aerosil ® 200 --.

In column 8, line 18, between "114.97" and "459.8", replace the number "227.91" with -- 229.91 --.

Signed and Sealed this
Eighth Day of January, 2013

David J. Kappos
*Director of the United States Patent and Trademark Office*

UNITED STATES PATENT AND TRADEMARK OFFICE
CERTIFICATE OF CORRECTION

PATENT NO.        : 8,309,607 B2
APPLICATION NO.   : 12/279062
DATED             : November 13, 2012
INVENTOR(S)       : Julia Schulze-Nahrup et al.

It is certified that error appears in the above-identified patent and that said Letters Patent is hereby corrected as shown below:

On the title page, item (75) (Inventors), replace the name "Kraass" with --Kraahs--.

Signed and Sealed this
Nineteenth Day of March, 2013

Teresa Stanek Rea
*Acting Director of the United States Patent and Trademark Office*